United States Patent
Heaton et al.

(10) Patent No.: US 9,339,490 B2
(45) Date of Patent: *May 17, 2016

(54) METHODS AND COMPOSITIONS FOR INCREASING SEX STEROIDS AND GROWTH HORMONES

(71) Applicant: Quality IP Holdings, LLC, Carson City, NV (US)

(72) Inventors: Amy L. Heaton, Salt Lake City, UT (US); Mitchell K. Friedlander, Salt Lake City, UT (US); Dennis Gay, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 14/301,219

(22) Filed: Jun. 10, 2014

(65) Prior Publication Data

US 2014/0302182 A1    Oct. 9, 2014

Related U.S. Application Data

(63) Continuation of application No. 13/623,105, filed on Sep. 19, 2012, now Pat. No. 8,747,922.

(51) Int. Cl.
| | | |
|---|---|---|
| *A61K 36/53* | (2006.01) | |
| *A61K 36/00* | (2006.01) | |
| *A61K 47/00* | (2006.01) | |
| *A61K 9/00* | (2006.01) | |
| *A61K 9/14* | (2006.01) | |
| *A61K 31/4015* | (2006.01) | |
| *A61K 36/538* | (2006.01) | |
| *A61K 31/198* | (2006.01) | |
| *A23L 1/30* | (2006.01) | |
| *A23L 1/305* | (2006.01) | |

(52) U.S. Cl.
CPC ........... *A61K 31/4015* (2013.01); *A23L 1/3002* (2013.01); *A23L 1/3051* (2013.01); *A61K 31/198* (2013.01); *A61K 36/538* (2013.01)

(58) Field of Classification Search
None
See application file for complete search history.

(56) References Cited

U.S. PATENT DOCUMENTS

| | | | |
|---|---|---|---|
| 4,224,316 A | 9/1980 | Momany | |
| 4,745,124 A * | 5/1988 | Ryan et al. | 514/362 |
| 6,071,926 A | 6/2000 | Van Cauter et al. | |
| 6,346,264 B1 | 2/2002 | White | |
| 6,368,617 B1 | 4/2002 | Hastings et al. | |
| 6,517,832 B1 | 2/2003 | Marrongelle et al. | |
| 6,974,841 B1 | 12/2005 | Rapisarda | |
| 7,790,683 B2 | 9/2010 | Grasso et al. | |
| 8,551,542 B1 | 10/2013 | Heaton et al. | |
| 8,715,752 B2 | 5/2014 | Heaton et al. | |
| 8,722,114 B2 | 5/2014 | Heaton et al. | |
| 8,722,115 B2 | 5/2014 | Heaton et al. | |
| 8,734,864 B2 | 5/2014 | Heaton et al. | |
| 8,747,921 B2 | 6/2014 | Heaton et al. | |
| 8,747,923 B2 | 6/2014 | Heaton et al. | |
| 8,765,195 B2 | 7/2014 | Heaton et al. | |
| 2002/0165343 A1 | 11/2002 | Martinez et al. | |
| 2003/0068309 A1 | 4/2003 | De Simone | |
| 2004/0063608 A1 | 4/2004 | Mowrey et al. | |
| 2004/0122234 A1 | 6/2004 | Hauser et al. | |
| 2007/0286909 A1 | 12/2007 | Smith et al. | |
| 2008/0050777 A1 | 2/2008 | Buechler et al. | |
| 2010/0047364 A1 | 2/2010 | Moneymaker et al. | |
| 2010/0186121 A1 | 7/2010 | Unkefer et al. | |
| 2011/0052754 A1 | 3/2011 | Foley | |
| 2011/0081329 A1 | 4/2011 | Smith et al. | |
| 2014/0079822 A1 | 3/2014 | Heaton et al. | |
| 2014/0079823 A1 | 3/2014 | Heaton et al. | |
| 2014/0079830 A1 | 3/2014 | Heaton et al. | |
| 2014/0079832 A1 | 3/2014 | Heaton et al. | |
| 2014/0080887 A1 | 3/2014 | Heaton et al. | |
| 2014/0080888 A1 | 3/2014 | Heaton et al. | |
| 2014/0212388 A1* | 7/2014 | Prieto | 424/93.4 |

FOREIGN PATENT DOCUMENTS

| | | |
|---|---|---|
| CN | 1243745 A | 2/2000 |
| GB | 9822333 | 12/1998 |
| KR | 1020000000757 A | 1/2000 |
| RU | 2429001 C1 | 9/2011 |
| WO | 9528854 A2 | 11/1995 |
| WO | 2004112511 A2 | 12/2004 |
| WO | 2007095618 A3 | 10/2007 |

OTHER PUBLICATIONS

Alba-Roth et al.; Arginine Stimulates Growth Hormone Secretion by Suppressing Endogenous Somatostatin Secretion; Journal of Clinical Endocrinology and Metabolism, vol. 67, No. 6, 1988; 1186-1189.

Albert et al.; Low-Dose Recombinant Human Growth Hormone as Adjuvant Therapy of Lifestyle Modifications in the Management of Obesity; Journal of Clinical Endocrinology & Metabolism 89(2) 695-704; 2004.

Bernardi et al.; Somatotropic axis and body weight in pre-menopausal and post-menopausal women: evidence for a neuroendocrine derangement, in absence of changes of insulin-like growth factor binding protein concentrations; Human Reproduction vol. 12, No. 2 pp. 279-287, 1998.

Bidlingmaier et al.; Growth Hormone; Handbook of Experimental Pharmacology 195; 2010; pp. 187-200.

Bjorntorp, et al.; Hypothalamic Origin of the Metabolic Syndrome X; Annals New York Academy of Sciences, pp. 297-307; 1999.

Bjorntorp, P.; Do Stress reactions cause abdominal obesity and comorbidities?; The International Association for the Study of Obesity, Obesity reviews; 2 73-85; 2001.

Bjorntorp, P.; The regulation of adipose tissue distribution in humans; International Journal of Obesity (1996) 20, 191-302.

Blackman et al.; Growth Hormone and Sex Steroid Administration in Healthy Aged Women and Men a Randomized Controlled Trial; JAMA, Nov. 12, 2002—vol. 288, No. 18; pp. 2282-2292.

(Continued)

*Primary Examiner* — Chris R Tate
*Assistant Examiner* — Russell Fiebig
(74) *Attorney, Agent, or Firm* — Magleby Cataxinos & Greenwood

(57) ABSTRACT

Embodiments of the invention generally relate to methods and supplements for increasing sex steroids and human growth hormone in a human being.

9 Claims, 3 Drawing Sheets

(56) References Cited

OTHER PUBLICATIONS

Bredella, et al.; Peak Growth Hormone-Releasing Hormone—Arginine-Stimulated Growth Hormone iS Inversely Associated with Intramyocellular and Intrahepatic Lipid Content in Premenopausal Women with Obesity; J. Clin Endrocrinol Metab. Oct. 2009; 94(10): 3995-4002.
Carli et al.; Changes in the exercise-induced hormone response to branched chain amino acid administration; Eru. J. Appl. Physiology (1992) 64:272-277.
Chromiak et al.; Use of Amino Acids as Growth Hormone-Releasing Agents by Athletes; Nutrition 18:657-661, 2002.
Corpas et al.; Human Growth Hormone and Human Aging; Endocrine Reviews, vol. 14, No. 1; 1993; pp. 20-39.
Corpas et al.; Oral Arginine-Lysine Does not Increase Growth Hormone or Insulin-like Growth Factor-I in Old Men; Journal of Gerontology: 1993, vol. 48, No. 4, M128-M133.
Ding et al.; Novel serum protein biomarkers indicative of growth hormone doping in healthy human subjects; Preteomics 2011, 11, 3565-3571.
Fogelholm et al. Low-Dose Amino Acid Supplementation: No Effects on Serum Human Growth Hormone and Insulin in Male Weightlifters; International Journal of Sport Nutrition, 1993, 3, 290-297.
Gourmelen et al., Effet du chlorhydrate d'ornithine sur le taux plamatique de l'hormone de croissance (HGH); Annels D'Endocrinologie; pp. 526-528; 1972.
Hayes et al.; Recombinant Human Growth Hormone and Recombinant Human Insulin-Like Growth Factor I Diminish the Cataboloic Effects of Hypogonadism in Man: Metabolic and Molecular Effects; The Journal of Clinical Endocrinology & Metabolism; vol. 86, No. 5; 2001.
Hersch et al.; Growth hormone (GH)-releasing hormone and GH secretagogues in normal aging: Fountain of Youth or Pool of Tantalus?; Clinical Interventions in Aging 2008:3(1) 121-129.
Iranmanesh et al., Age and Relative Adiposity are Specific Negative Determinants of the Frequency and Amplitude of Growth Hormone (GH) Secretory Bursts and the Half-Life of Endogenous GH in Healthy Men; Journal of Clinical Endocrinology and Metabolism; vol. 73, No. 5; pp. 1081-1088.
Isidori et al.; A Study of growth hormone release in man after oral administration of amino acids; Current Medical Research and Opinion; vol. 7, No. 7, 1981; pp. 475-481.
Karlsson et al.; Effects of growth hormone treatment on the leptin system and on energy expenditure in abdominally obese men; European Journal of Endocrinology (1998) 138 408-414.
Kraemer et al.; Chronic Resistance training in women potentiates growth hormone in vivo bioactivity: characterization of molecular mass variants; Am. J. Physiol Endocrinol Metab 291: E1177-E1187, 2006.
Lambert et al.; Failure of Commercial Oral Amino Acid Supplements to Increase Serum Growth Hormone Concentrations in Male Body-Builders; International Journal of Sport Nutrition, 1993, 3, 298-305.
Legakis et al.; Human Galanin Secretion is Increased Upon Normal Exercise Test in Middle-Age Individuals; Endocrine Research 26(3), 357-365 (2000).
Maccario et al.; Relationships between IFG-I and age, gender, body mass, fat distribution, metabolic and hormonal variables in obese patients; International Journal of Obesity (1999) 23, 612-618.
Makimura et al.; The relationship between reduced testosterone, stimulated growth hormone secretion and increased carotid inimamedia thickness in obese men; Clin Endocrinol (Oxf). Nov. 2010; 73(5): 622-629.
Menagh et al.; Growth Hormone Regulates the Balance Between Bone Formation and Bone Marrow Adiposity; JBMR; vol. 25, No. 4, Apr. 2010, pp. 757-768.
Merimee et al.; Arginine-Initiated Release of Human Growth Hormone; The New England Journal of Medicine; Jun. 26, 1969; pp. 1434-1438.
Nindl et al.; Growth hormone pulsatility profile characteristics following acute heavy resistance exercise; J. Appl Physiol 91: 163-172, 2001.
O'Connor et al.; Interrelationships of Spontaneous Growth Hormone Axis Activity, Body Fat, and Serum Lipids in Healthy Elderly Women and Men; Metabolism, vol. 48, No. 11 Nov. 1999: pp. 1424-1431.
Papadakis et al.; Effect of growth hormone replacement on wound healing in healthy older men; Would Repair and Regeneration Oct.-Dec. 1996; pp. 421-425.
Papadakis et al.; Growth Hormone Replacement in Healthy Older Men Improves Body Composition but Not Functional Ability; Ann Intern Med. 1996; 124-: 708-716.
Pasquali et al.; Hormones and pathophysiology of obesity; Hormones and Obesity; 2001 pp. 9-20.
Pelsers et al.; Influence of Gender in Growth Hormone Status in Adults: Role of Urinary Growth Hormone; Clinical Chemistry 45, No. 3, 1999, pp. 443-444.
Perry, Horace M. III; The Endocrinology of Aging; Clinical Chemistry 45:8(B); 1369-1376 (1999).
Rubin et al.; New anabolic therapies in osteoporosis; Current Opinon in Reeumatology 2002, 14:433-440.
Rudman et al.; Effects of Human Growth Hormone in Men over 60 Years Old; The New England Journal of Medicine; vol. 323, Jul. 5, 1990; 6 pages.
Su et al.; Insulin-like growth factor 1 and hair growth; 1999 Dermatology Online Journal; 20 pages.
Suminski et al.; Acute Effect of Amino Acid Ingestion and Resistance Exercise on Plasma Growth Hormone Concentration in Young Men; International Journal of Sport Nutrition, 1997, 7, 48-60.
Twickler et al.; Adult-Onset Growth Hormone Deficiency: Relation of Postprandial Dyslipidemia to Premature Atherosclerosis; The Journal of Clinical Endocrinology & Metabolism 88(6): 2479-2488.
Vance, Mary L.; Growth Hormone for the Elderly?; The New England Journal of Medicine; Jul. 5, 1990; pp. 52-54.
White et al.; Effects of an Oral Growth Hormone Secretagogue in Older Adults; J. Clin Endocrin Metab.; 2009; 29 pages.
Zouboulis et al.; Intrinsische Hautalterung; Eine kritische Bewertung der Rolle der Hormone; Hautarzt 2003 54: 825-832.
Bae, O.; "A Chinese medicinal composition for stimulating growth hormone", KR 2000/000757 A, 2000, Abstract Only.
Boger, R. H., "The Pharmacodynamics of L-Arginine1-3", The Journal of Nutrition: 6th Amino Acid Assessment Workshop, 2007, pp. 1650S-1655S, vol. 137, American Society for Nutrition.
Chowen et al.; The regulation of GH secretion by sex steroids; European Journal of Endocrinology, 2004, pp. U95-U100, vol. 151, Society of the European Journal of Endocrinology.
Collier, S. R. et al., "Growth hormone responses to varying doses of oral arginine", Growth Hormone & IGF Research, 2005, vol. 15, pp. 136-139.
Cooper et al.; "Subclinical thyroid disease," Jan. 23, 2012, 13 pages.
Devesa et al.; "The Role of Sexual Steroids in the Modulation of Growth Hormone (GH) Secretion in Humans," J. Steroid Biochem. Molec. Biol., 1991,vol. 40—No. 1-3, pp. 165-173.
"External Wind", <http://www.tcvmherbal.com/JTDocs/Flyers/External%20Wind.pdf>, Downloaded from website Oct. 22, 2013, Jing Tang, 2 pages.
Farr et al.; "The antioxidants α-lipoic acid and N-acetylcysteine reverse memory impairment and brain oxidative stress in aged SAMP8 mice," Journal of Neurochemistry, 2003, vol. 84, pp. 1173-1183.
Fung, et al; "Schizonepeta tenuifolia: Chemistry, Pharmacology, and Clinical Applications," J. Clin. Pharmacal., 2002, vol. 42, pp. 30-36.
Gasco et al.; "Retesting the childhood-onset GH-deficient patient," European Journal of Endocrinology, vol. 159, 2008, pp. S45-S52.
Goto et al.; "Growth Hormone Receptor Antagonist Treatment Reduces Exercise Performance in Young Males", Sep. 2009, J Clin Endocrinol Metab, 94(9), pp. 3265-3272.
Grioli et al. "Pyroglutamic acid improves the age associated memory impairment," citation and abstract from Pyroglutamate, Jun. 13, 2002, Retrieved from the Internet on Apr. 9, 2013. Retrieved from: <http://web.archive.org/web/20020613031716/http://www.raysahelian.com/pyroglutamate.html>, 1 page.
Grunfeld et al.; "The Acute Effects of Human Growth Hormone Administration on Thyroid Function in Normal Men," Journal of Clinical Endocrinology and Metabolism, 1988, vol. 67—No. 5, pp. 1111-1114.
Hansen et al.; Effects of 2 wk of GH administration on 24-h indirect calorimetry in young, healthy, lean men; Am. J. Physiol Endocrinol Metab 289: E1030-E1038, 2005.

(56) References Cited

OTHER PUBLICATIONS

Ho et al.; "The Pharmacokinetics, Safety and Endocrine Effects of Authentic Biosynthetic Human Growth Hormone in Normal Subjects", Clinical Endocrinology, 1989, vol. 30, pp. 335-345.
Kim et al.; "Anti-Inflammatory Activity of Schizonepeta tenuifolia through the Inhibition of MAPK Phosphorylation in Mouse Peritoneal Macrophages," The American Journal of Chinese Medicine, vol. 36—No. 6, pp. 1145-1158.
King, J.; "What is L-Arginine HCL?", <http://www.livestrong.com/article/464027-what-is-l-arginine-hcl/>, Jun. 5, 2011, 6 pages.
Leelarungrayub et al.; "N-Acetylcysteine Supplementation Controls Total Antioxidant Capacity, Creatine Kinase, Lactate, and Tumor Necrotic Factor-Alpha against Oxidative Stress Induced by Graded Exercise in Sedentary Men," Oxidative Medicine and Cellular Longevity. vol. 2011, Article ID 329643, 7 pages.
"L-Lysine," <http://www.ironmagazineforums.com/threads/149021-L-Lysine>, Retrieved from the Internet on: Jul. 15, 2014, 7 pages.
Maggi et al.; "Hormonal Causes of Male Sexual Dysfunctions and Their Management (Hyperprolactinemia, Thyroid Disorders, GH Disorders, and DHEA)," International Society for Sexual Medicine, 2012, 9 pages.
Mayo Clinic Staff; "Post-traumatic stress disorder (PTSD)," <http://www.mayoclinic.org/diseases-conditions/post-traumatic-stress-disorder/basics/definition/con-20022540>, Apr. 15, 2014.
Millea, P. J.; "N-Acetylcysteine: Multiple Clinical Applications," American Family Physician, Aug. 1, 2009, vol. 80—No. 3, pp. 265-269.
Moller et al.; "Effects of Growth Hormone Administration on Fuel Oxidation and Thyroid Function in Normal Man," Metabolism, vol. 41—No. 7, Jul. 1992, pp. 728-731.
Reid et al.; "N-Acetylcysteine Inhibts Muscle Fatigue in Humans," J. Clin. Invest., vol. 94, Dec. 1994, pp. 2468-2474.
Pryor, et al.; "Growth Hormone: Amino Acids as GH secretagogues," <http://www.vrp.com/amino-acids/amino-acids/growth-hormone-amino-acids-as-gh-secretagogues-a-review-of-the-literature>, Retrieved Jul. 16, 2014, 5 pages.
Kim et al.; "Anti-Inflammatory Activity of Schizonepeta tenuifolia through the Inhibition of MAPK Phosphorylation in Mouse Peritoneal Macrophages," The American Journal of Chinese Medicine, vol. 36—No. 6, 2008, pp. 1145-1158.
Anonymous, "Dr. Oz Human Growth Hormone HGH the Pursuit of Youth and Beauty," Oct. 13, 2011, retrieved from the internet: URL:http://healthybodydaily.com/dr-oz-in-case-you-missed-it/dr-oz=hgh-human-growth-hormone (retrieved on Sep. 15, 2014).
Anonymous, "Animal Outreach," Aug. 18, 2012, retrieved from the internet: URL: http://animal-outreach.org/2012/08 (retrieved on Sep. 15, 2014).
Extended European Search Report for application No. 13823912.4-1464/2744490, based on PCT/US2013060645, 4 pages.
Brigitte Mars. Internet Publication Date: Mar. 1, 2009 [Retrieved from the Internet on: Jul. 31, 2014]. Retrieved from: <URL: http://brigittemars.com/articles/herbal-natural-remedies/treating-headaches-naturally/>.
"MedlinePlus: L-arginine". Internet Archive Datae:Oct. 5, 2010 [Retrieved from the Internet on: Jul. 31, 2014]. Retrieved from: <URL: http://www.nlm.nih.gov/medlineplus/druginfo/natural/875.html>.
Pavel et al.; "Impact of Growth Hormone on Central Nervous Activity, Vigilance, and Tiredness after Short-Term Therapy in Growth Hormone-Deficient Adults," Horm. Metab. Res., 2003, vol. 35, pp. 114-119.
Oliveira, et al.; "Free Amino Acids of Tronchuda Cabbage (*Brassica oleracea* L. var. costata DC): Influence of Leaf Position (Internal or External) and Collection time", Journal of Agricultural and Food Chemistry, 2008, vol. 56, pp. 5216-5221.
Pradines-Figueres et al.; "Transcriptional control of the expression of lipoprotein lipase gene by growth hormone in preadipocyte Ob1771 cells," Journal of Lipid Research, vol. 31, 1990, pp. 1283-1291.
Silber et al.; "Growth and Maintenance of Dogs Fed Amino Acids as the Source of Dietary Nitrogen," The Journal of Nutrition, Oct. 11, 1948, pp. 429-441.
Roddick, J.; "Sleep Disorders," <http://www.healthline.com/health/sleep/disorders#Overview 1>, Retrieved from the Internet on Jul. 16, 2014, 3 pages.
Rudman et al.; "The Short Child with Subnormal Plasma Somatomedin Cl," Pediatric Research, vol. 19—No. 10, 1985, pp. 975-980.
Russell et al.; "Free Triiodothyronine has a distinct circadian rhythm that is delayed but parallels thyrotropin levels," J. Clin Endocrin Metab., Mar. 25, 2008, 22 pages.
Sahley, B J. "Amino Acid Brain Boosters" <http://www.teenlinkusa.com/aminoacids2.html>, Retrieved on Jul. 16, 2014, 4 pages.
Salomon et al.; "The Effects of Treatment with Recombinant Human Growth Hormone on Body Composition and Metabolism in Adults with Growth Hormone Deficiency," New England Journal of Medicine, Dec. 28, 1998, vol. 321—No. 26, pp. 1797-1803.
"Schizonepeta Tenuifolia," <http://examine.com/supplements/Schizonepeta+tenuifolia/>, Sep. 30, 2013, 12 pages.
Schwartz et al., "Hormone Replacement Therapy in the Geriatric Patient: Current State of the Evidence and Questions for the Future. Estrogen, Progesterone, Testosterone, and Thyroid Hormone Augmentation in Geriatric Clinical Practice: Part 1," Clin Geriatr Med vol. 27, 2011, pp. 541-559.
Schwartz et al., "Hormone Replacement Therapy in the Geriatric Patient: Current State of the Evidence and Questions for the Future. Estrogen, Progesterone, Testosterone, and Thyroid Hormone Augmentation in Geriatric Clinical Practice: Part 2," Clin Geriatr Med, vol. 27, 2011, pp. 561-575.
Sen et al.; "Exercise-induced oxidative stress: glutathione supplementation and deficiency," J. Appl. Physiol., vol. 77, 1994, pp. 2177-2187.
Sen et al.; "Oxidative stress after human exercise: effect of N-acetylcysteine supplementation," J. Appl. Physiol., vol. 76, 1994, pp. 2570-2577.
Sen, C. K.; "Glutathione homeostasis in response to exercise training and nutritional supplements," 1999, Molecular and Cellular Biochemistry, vol. 196, pp. 31-42.
Sevigny et al.; "Growth hormone secretagogue MK-677: No clincical effect on AD progression in a randomized trial," American Academy of Neurology, 2008, vol. 71, pp. 1702-1708.
Smith et al.; "Sleep Disorders and Sleeping Problems," <http://www.helpguide.org/life/sleep_disorders.htm>, Jun. 2014, Helpguide.org, 7 pages.
Tarantini et al.; "Serum ghrelin levels in growth hormone-sufficient and growth hormone-deficient patients during growth hormone-releasing hormone plus arginine test," J. Endocrinol. Invest. vol. 32, pp. 335-337, 2009.
Tavakkolizadeh et al.; "Effect of Growth Hormone on Intestinal NA+/Glucose Cotransporter Activity," Journal of Parenteral and Enteral Nutrition, vol. 25, No. 1, Mar. 2000, pp. 18-22.
Topo et al.; "The role and molecular mechanism of D-aspartic acid in the release and synthesis of LH and testosterone in humans and rats," Reproductive Biology and Endocrinology, Oct. 27, 2009, 11 pages.
Van Cauter et al.; "Metabolic consequences of sleep and sleep loss," Sleep Medicine 9 Suppl. 1, 2008, pp. S23-S28.
Van Liempt et al.; "Decreased nocturnal growth hormone secretion and sleep fragmentation in combat-related posttraumatic stress disorder; potential predictors of impaired memory consolidation," Psychoneuroendocrinology, 2011, vol. 36, pp. 1361-1369.
Vermeulen et al., "Testosterone, body composition and aging," J. Endocrinol. Invest., vol. 22, pp. 110-116, 1999.
Weikel et al.; "Ghrelin promotes slow-wave sleep in humans," Am J. Physiol Endocrinol Metab, vol. 284, pp. E407-E415, 2003.
Weizman et al.; "Impact of the Gulf War on the Anxiety, Cortisol, and Growth Hormone Levels of Israeli Civilians," Am J. Psychiatry, vol. 151—No. 1, Jan. 1994, pp. 71-75.
Welbourne, T. C.; "Increased plasma bicarbonate and growth hormone after an oral glutamine load 81-3," The American Journal of Clinical Nutrition, 1995, vol. 61, pp. 1058-1061.
Yen et al.; "Aging and the Adrenal Cortex," Experimental Gerontology, vol. 33, Nos. 7/8, pp. 897-910, 1998.
Yuen et al.; "Is Lack of Recombinant Growth Hormone (GH)-Releasing Hormone in the United States a Setback or Time to Consider Glucagon Testing for Adult GH Deficiency?", J. Clin, Endocrinol Metab, Aug. 2009, vol. 94—No. 8, pp. 2702-2707.

\* cited by examiner

METHODS AND COMPOSITIONS FOR INCREASING SEX STEROIDS AND GROWTH HORMONES

CROSS-REFERENCE TO RELATED APPLICATION

This application is a continuation/divisional of U.S. patent application Ser. No. 13/623,105, filed Sep. 19, 2012, now U.S. Pat. No. 8,747,922 issued on Jun. 10, 2014, the disclosure of which is hereby incorporated herein in its entirety by this reference.

FIELD OF THE DISCLOSURE

The present disclosure generally relates to methods and supplements for improving health in a subject. In some embodiments, a nutritional supplement may be administered to a subject to increase levels of growth hormone (GH) and sex hormone (e.g., testosterone) in the subject.

BACKGROUND

The primary biological function of human growth hormone (hGH) includes stimulating growth, cell repair and regeneration. Once the primary growth period of adolescence concludes, the primary function of hGH in adulthood becomes that of cell regeneration and repair, helping regenerate skin, bones, heart, lungs, liver and kidneys to their optimal, youthful cell levels. As is the case with many of our other hormones or their pre-cursors, such as testosterone, estrogen, progesterone, DHEA and melatonin, hGH levels decline with age. Therapeutically, many of these hormones can be replaced to offset some of the effects of aging such as menopausal symptoms in women or erectile dysfunction in men.

The human body, like every other living entity, works on daily, or circadian, as well as monthly and annual rhythms. Daily growth hormone secretion diminishes with age with roughly half the levels at age forty that we had when we were twenty, and about one-third of those youthful levels at age sixty. In some sixty-year olds, the levels are as low as 25% of the hGH levels in a twenty-year old. Symptoms of aging include loss of muscle, increase of fat, decreased physical mobility, decreased energy levels and as a result, diminished socialization, diminished healing ability and an increased risk of cardiovascular disease and decreased life expectancy. Low hGH levels are associated with the aging process and early onset of disease. For example, Rosen and Bengtsson noted an increased death rate from cardiovascular disease in hGH deficient patients. (Rosen, T., Bengtsson, B. A., Lancet 336 (1990): 285-2880)

Until recently, hGH was available only in expensive injectable forms, and benefits from the restoration of hGH levels available only to those with the ability to pay. Most recently substances that can trigger the release of human growth hormone from an individual's own anterior pituitary gland have become available. These are generically referred to as secretagogues. Secretagogues have the ability to restore hGH levels, potentially to the levels found in youth. See, e.g., "Grow Young With hGH" by Dr. Ronald Klatz, President of the American Academy of Anti-Aging, published in 1997 by Harper Collins.

HGH-deficient adults have marked reductions in lean body mass, and within months of hGH treatment, gains in lean body mass, skin thickness and muscle mass are observed. (Cuneo R C et al. J Appl Physiol 1991; 70:695-700; Cuneo R C et al. J Appl Physiol 1991; 70:688-694; Rudman D et al. N Engl J Med 1969; 280:1434-1438).

It is well-established that intravenous (IV) administration of some amino acids results in significant hGH secretion. Intravenous infusion of 183 mg of arginine/kg body weight in females increased hGH levels >20-fold and 30 g of arginine elevated serum hGH levels 8.6 fold in males (Merimee T J et al. N Engl J Med 1969; 280:1434-1438; Alba-Roth J et al. J Clin Endocrinol Metab 1988; 67:1186-1189). Other amino acids, such as methionine, phenylalanine, lysine, histidine, and ornithine have also led to marked increases in hGH (Alba-Roth, Muller, Schopohl, & von Werder, 1988; Chromiak & Antonio, 2002; Gourmelen, M., M. Donnadieu, et al. (1972) Ann Endocrinol (Paris) 33(5): 526-528).

Given the difficulties in IV administration of amino acids for widespread use, interest in elucidating the hGH response to oral amino acid supplements prompted testing of such supplements containing mainly arginine, lysine and ornithine at varying amounts. Yet the pronounced variability in results among these studies make clear the complexities involved in the design of an effective supplement for supporting hGH levels in the general public. (Suminski R R et al. Int J Sport Nutr 1997; 7:48-60; Lambert M I et al. Int J Sport Nutr 1993; 3:298-305; Corpas E et al. J Gerontol 1993; 48:M128-M133; Isidori A et al. Curr Med Res Opin 1981; 7:475-481; Fogelholm G M et al. Int J Sport Nutr 1993; 3:290-297; Chromiak J A, Antonio J. Nutrition 2002 July; 18(7-8):657-61).

Testosterone is a steroid hormone synthesized from cholesterol and occurs in both bound and unbound (free) forms in the body. (Feldman et al., 2002) Though present in small amounts in females, this hormone determines sexuality in men and hence is considered the male sex hormone. Low testosterone levels in men can have adverse effects such as incomplete sexual development, reduced libido, decreased muscle mass and strength, loss of body hair, gynecomastia (the term for abnormal mammary gland development in men relating to breast enlargement), impaired spermatogenesis, and underdeveloped testes. (Salenave, Trabado, Maione, Brailly-Tabard, & Young, 2012) The levels of testosterone in men are shown to decrease with increasing age. Total testosterone levels are said to decline at a rate of 1.6% per year, and levels of bioavailable testosterone are reduced by approximately 2-3% per year according to the longitudinal results obtained from the Massachusetts Male Aging Study. (Feldman et al., 2002).

Serum hGH levels differ in relation to various factors including age, gender, hormone status, and BMI. (Iranmanesh, Lizarralde, & Veldhuis, 1991); (Chowen, Frago, & Argente, 2004) The effect of the sex hormones on hGH becomes clear in the maturation process most obviously at puberty, wherein sex hormones have both organizational and activational effects related to hGH synthesis. ((Chowen et al., 2004) Testosterone treatment in testosterone-deficient men has been shown to increase hGH secretion. (Liu, Merriam, & Sherins, 1987) Furthermore, testosterone administration in normal men also increases growth hormone releasing hormone (GHRH) induced hGH secretion, (Devesa et al., 1991; Hobbs, Plymate, Rosen, & Adler, 1993) signifying the association between the endocrine axes of these two hormones.

However, the locus and mechanism by which sex steroids contribute to the modulation of GH secretion in humans is not clearly understood. Devesa et al. (1991) J. Steroid Biochem. Mol. Biol. 40(1-3):165-73. Secretion of GH from the pituitary gland is episodic, and dependent upon, inter alia, the episodic release of growth hormone releasing hormone (GHRH) and somatostatin. Id. GH secretion may be determined by a balance of contradictory effects of different sex hormones. For example, inhibitory effects of 17β-estradiol and stimulatory effects of testosterone with regard to hypothalamic somatostatin release may act in concert to modulate GH secretion. Id.

BRIEF SUMMARY OF THE DISCLOSURE

Described herein are nutritional supplements and methods for using the same. In embodiments, the nutritional supplement may be an amino acid secretagogue composition, which, when administered orally, stimulates the pituitary gland of a subject to release growth hormone (e.g., hGH), and results in the release of testosterone from the testes.

Some embodiments include an oral nutritional supplement that comprises, for example and without limitation: L-arginine, Oxo-proline, L-lysine, and cysteine. Particular examples include an oral nutritional supplement that consists essentially of L-arginine hydrochloride, Oxo-proline, L-lysine hydrochloride, N-acetyl-L-cysteine, L-glutamine, and schizonepeta powder.

Certain embodiments herein include an oral nutritional supplement dosage form that consists of 0.86 mmol L-arginine; 1.32 mmol Oxo-proline; 2.05 mmol L-lysine; 1.53 μmol N-acetyl L-cysteine; 1.71 μmol L-glutamine; and 125 μg Schizonepta (aerial parts) powder. This oral nutritional supplement is referred to herein as "SeroVital™." SeroVital™ may be orally administered in an amount of, for example, 2.9 grams (i.e., 4 unit dosage forms) to a human being, so as to stimulate the release of hGH and/or increase testosterone levels in the human being. The nutritional supplement may be administered on a regular basis, such as a weekly or monthly intake at a dosage tailored to the subject's needs; i.e., the nutritional supplement may be administered regularly as multiples (1×, 2×, etc.) of the structural units (pills, tablets, capsules, etc.) in accordance with the needs of the subject.

Some embodiments include a method for jointly increasing growth hormone (e.g., hGH) and androgen (e.g., testosterone) levels in a subject (e.g., a human subject) that comprises administering (e.g., orally) a nutritional supplement to a subject to improve one or more objective health metrics, including for example and without limitation: increasing lean body mass; reducing obesity, adipose tissue mass, and anxiety; supporting weight loss; decreasing appetite and atrophic processes in skeletal muscle, liver, kidney, spleen, skin, and bone; and improving at least one of energy, endurance, sleep, metabolism, heart rate, blood pressure, cardiovascular health, sympathetic nervous activity, thyroid response, glucose utilization, mental/cognitive function, reaction time, bone density, hair health and appearance, nail health and appearance, skin health and appearance, libido, and at least one androgen-mediated condition(s).

DETAILED DESCRIPTION

Figure 1:
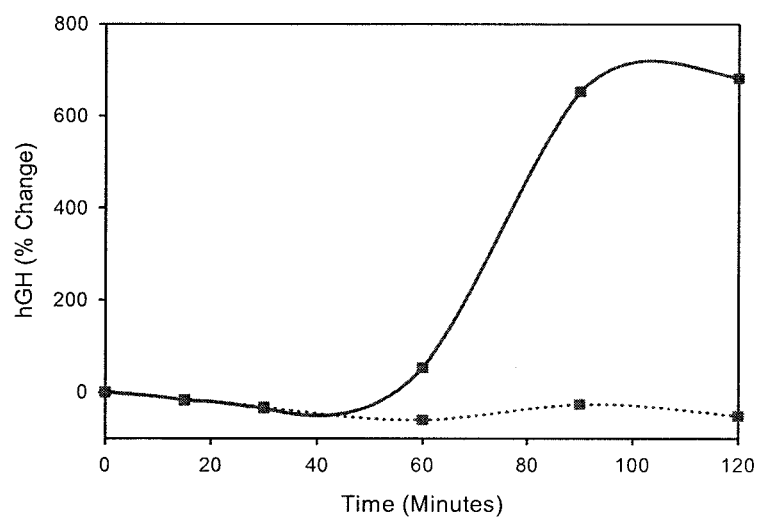
FIG. 1 includes a plot of growth hormone levels measured in subjects after administration of an exemplary supplement compared to a placebo.

The determination of an effective and safe oral functional blend that stimulates hGH secretion in the general population is important, since athletes, entertainers, and now the general public, seek effective hGH support supplements and understand hGH to have rejuvenating properties. Indeed, once partial to athletes and entertainers, the desire for effective supplements to provoke hGH increases now extends to the general public. Not only do they have a goal of building lean tissue and reducing fat, but also of improving skin quality and providing other rejuvenating qualities that hGH is understood to provide. However, the literature on oral amino acids for use in stimulating hGH does not contain clear evidence for an optimized oral amino acid-containing blend able to stimulate hGH in the general public, including both men and women of a wide age range.

The original and primary therapeutic use of testosterone was for the treatment of men with low levels endogenous testosterone production. According to this use, serum testosterone levels are brought to and maintained in a normal range. However, testosterone may also be desirably increased in a subject for one of many other conditions and purposes besides replacement. For example and without limitation, testosterone therapy may be desired to reduce infertility; increase libido and/or correct erectile dysfunction; treat osteoporosis; encourage penile enlargement; encourage height growth; encourage bone marrow stimulation; reversing the effects of anemia; and increase appetite. Testosterone therapy may be particularly desirable in aging individuals exhibiting decreased androgen production.

Embodiments herein provide a nutritional supplement for jointly elevating growth hormone (e.g., hGH) and testosterone release. Particular embodiments provide an amino acid-containing composition that is well tolerated, and may have the result of increasing or elevating hGH release in those individuals whose hGH release rates have slowed as a function of increasing age, or that have normal hGH levels but desire higher hGH levels. Compositions may also have the result of increasing or elevating testosterone levels. There is a need for a nutritional supplement that efficiently and demonstrably enhances the production and effects of natural human growth hormone and testosterone individuals of the general population.

Some embodiments herein provide a nutritional supplement for use by a human being. In particular embodiments, the nutritional supplement is an amino acid secretagogue composition, which, when administered orally, may stimulate the pituitary gland to produce hGH, and may jointly stimulate the testes to produce testosterone.

Increased production of hGH may result in inhibition of insulin depression; inhibition of hyperglycemia and increase in insulin effectiveness; enhancement of fat conversion; lowering of cholesterol; and/or normalization of lipid balance. Increased production of testosterone may result in modulation of physiological or pathological conditions mediated by androgens and the interaction of androgens with their receptors. In examples, a supplement herein may function as a dietary supplement by assisting the body's own ability to secrete hGH and testosterone naturally, and in a manner which is safe and effective. Such a supplement may provide growth hormone therapy and testosterone therapy in a more affordable manner than existing compositions and methods, for example, injectable steroid compositions.

Particular embodiments herein include an oral nutritional supplement that comprises L-lysine, L-arginine, oxo-proline, and one of cysteine and glutamine. In some examples, a supplement herein may comprise both cysteine and glutamine and/or schizonepeta powder. In particular examples, a functional dosage includes the L-arginine at a level between about 0.1-6 mmol and the oxo-proline between about 0.1-8 mmol, and/or the L-lysine in an amount between about 0.1-12 mmol. In particular examples, the cysteine and/or glutamine may be contained at a level between about 0.001-6 mmol.

Cysteine may be present in a supplement according to particular embodiments as n-acetyl L-cysteine, and the glutamine may be L-glutamine. Amino acids in a nutritional supplement herein may be delivered as non-toxic salts thereof, effective complexes thereof, stable chelates thereof, active esters thereof, functional derivatives thereof, and mixtures thereof which are effective to increase hGH levels in a subject from the general population.

Particular embodiments herein include an oral nutritional supplement that consists essentially of L-lysine (e.g., L-lysine HCl), L-arginine (e.g., L-arginine HCl), oxo-proline, N-acetyl-L-cysteine, L-glutamine, and schizonepeta (aerial parts) powder. In particular examples, a functional dosage includes L-arginine at a level between about 0.1-6 mmol and oxo-proline between about 0.1-8 mmol, and/or L-lysine in an amount between about 0.1-12 mmol. n-acetyl L-cysteine and/or L-glutamine may be comprised in some exemplary supplements at a level between about 0.001-6 mmol. In particular examples, a functional dosage includes L-arginine at a level between about 2.5-4.5 mmol and oxo-proline between about 4-6 mmol, and/or L-lysine in an amount between about 7-9 mmol. N-acetyl L-cysteine and/or L-glutamine may be comprised in some exemplary supplements at a level between about 0.001-0.5 mmol.

Certain embodiments herein include an oral nutritional supplement dosage form that consists of 0.86 mmol L-arginine; 1.32 mmol Oxo-proline; 2.05 mmol L-lysine; 1.53 µmol N-acetyl L-cysteine; 1.71 µmol L-glutamine; and 125 µg Schizonepta (aerial parts) powder (SeroVital™). Thus, an oral nutritional supplement dosage form may consist of 181.38 mg L-arginine HCl; 170.93 mg L-pyroglutamic acid; 374.83 mg L-lysine HCl; 0.25 mg N-acetyl L-cysteine USP; 0.25 mg L-glutamine; and 0.125 mg Schizonepta (aerial parts) powder, for example, in a capsule. In some examples, the oral nutritional supplement may be administered to a human being by orally administering 4 such dosage forms (i.e., 725.50 mg L-arginine HCl; 683.70 mg L-pyroglutamic acid; 1499.30 mg L-lysine HCl; 1.00 mg N-acetyl L-cysteine USP; 1.00 mg L-glutamine; and 0.50 mg Schizonepta (aerial parts) powder).

Some embodiments herein provide a method for increasing human growth hormone and/or testosterone in humans that comprises orally administering a nutritional supplement for jointly elevating growth hormone release and testosterone release to a healthy human being. As used herein, a "healthy human being" refers to a human being having any age-related decline in hGH and/or testosterone, excluding any physiological deficiency that is not age-related. Particular embodiments include oral administration of a nutritional supplement for jointly elevating growth hormone release and testosterone release to a human that is at least 30 years old.

A nutritional supplement for jointly elevating growth hormone release and testosterone release may be orally administered to a human being to improve health, including by: increasing lean body mass; reducing obesity, adipose tissue mass, and anxiety; supporting weight loss; decreasing appetite and atrophic processes in skeletal muscle, liver, kidney, spleen, skin, and bone; and improving energy, endurance, sleep, metabolism, heart rate, blood pressure, cardiovascular health, sympathetic nervous activity, thyroid response, glucose utilization, mental/cognitive function, reaction time, bone density, hair health and appearance, nail health and appearance, skin health and appearance, and libido.

In certain examples, oral administration of a nutritional supplement for jointly elevating growth hormone release and testosterone release may improve hair and/or nail thickness, length, and/or growth. Oral administration of a nutritional supplement for jointly elevating growth hormone release and testosterone release may improve wound healing, provide anti-aging skin properties, reduce wrinkles, dark spots, discolorations, dullness, sagging, laxity, and thinning, and may further improve texture, luminosity, "lift," tone, radiance, smoothness, uniformity, and youthful look of skin.

A nutritional supplement for jointly elevating growth hormone release and testosterone release may be orally administered to a human being to improve health by affecting one or more condition(s) and/or disease(s) that depend upon androgen activity. Such conditions and diseases include, for example and without limitation: maintenance of muscle strength and function; reversal or prevention of frailty or age-related functional decline ("ARFD") in the elderly (e.g., sarcopenia); remediation of age-related decreased testosterone levels in men; treatment of male menopause; treatment of hypogonadism; male hormone replacement; treatment of male and female sexual dysfunction (e.g., erectile dysfunction, decreased sex drive, sexual well-being, decreased libido); male and female contraception; hair loss; Reaven's Syndrome; enhancement of bone and muscle performance/strength; treatment of catabolic side effects of glucocorticoids; prevention and/or treatment of reduced bone mass, density, and/or growth (e.g., osteoporosis and osteopenia); treatment of chronic fatigue syndrome (CFS); chronic myalgia; treatment of acute fatigue syndrome and muscle loss following elective surgery; acceleration of wound healing; acceleration of bone fracture repair; prevention of post-surgical adhesion formation; acceleration of tooth repair or growth; maintenance of sensory function (e.g., hearing, sight, olfaction and taste); treatment of periodontal disease; treatment of wasting secondary to fractures and wasting in connection with, for example, chronic obstructive pulmonary disease (COPD), chronic liver disease, AIDS, weightlessness, cancer cachexia, burn and trauma recovery, chronic catabolic state, eating disorders, and chemotherapy; treatment of cardiomyopathy; treatment of thrombocytopenia; treatment of one or more symptoms of Crohn's disease; treatment of short bowel syndrome; treatment of irritable bowel syndrome; treatment of inflammatory bowel disease; treatment of ulcerative colitis; treatment of complications associated with transplantation; treatment of physiological short stature; treatment of obesity and growth retardation associated with obesity; treatment of anorexia (e.g., associated with cachexia or aging); treatment of hypercortisolism and Cushing's syndrome; treatment of Paget's disease; treatment of osteoarthritis; induction of pulsatile growth hormone release; treatment of osteochondrodysplasias; treatment of depression, nervousness, irritability, and stress; treatment of reduced mental energy and low self-esteem (e.g., motivation/assertiveness); improvement of cognitive function (e.g., treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering of blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reduction of cachexia and protein loss due to chronic illness such as cancer or AIDS; treatment of hyperinsulinemia, including nesidioblastosis; treatment of immunosuppressed patients; treatment of wasting in connection with multiple sclerosis or other neuro-degenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM; treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy; treatment of muscular atrophy; treatment of musculoskeletal impairment; improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasias of the prostate (e.g., advanced metastatic prostate cancer) and malignant tumor cells including the androgen receptor, such as is the case for breast, brain, skin, ovarian, bladder, lymphatic, liver and kidney cancers; treatment of cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor; treatment of premenstrual syndrome; and treatment of vaginal dryness.

A nutritional supplement for jointly elevating growth hormone release and testosterone release may be used in combination with other hormone and/or steroid modulating supplements to enhance the effect of the nutritional supplements disclosed herein.

In accordance with the "consist essentially of" and "consisting essentially of" language herein, a nutritional supplement for jointly elevating growth hormone release and testosterone release in some embodiments is essentially limited to the aforementioned ingredients, and does not include any additional active ingredients intended to add nutritional content (e.g., vitamins, minerals, etc.), but may include additional ingredients not intended to add nutritional content, for example, ingredients intended to fulfill a non-nutritional purpose (e.g., coloring, fillers, flavoring, an ingredient for maintaining the structural form, etc.).

Each ingredient of a nutritional supplement for jointly elevating growth hormone release and testosterone release may be prepared in accordance with any method known to one of ordinary skill in the art. Alternatively, each ingredient may be obtained in a fully-prepared from a commercially available source.

A nutritional supplement for jointly elevating growth hormone release and testosterone release may be in any suitable oral administration form, including but not limited to: a chewable form, a liquid form, a spray form, a capsule form, a suppository form, dissolvable wafer, and a powder form. In some embodiments, a dosage form of the nutritional supplement may be present in an amount of about 2.9 grams.

Irrespective of the structural form of the nutritional supplement for jointly elevating growth hormone release and testosterone release, the ingredients of the nutritional supplement may be distributed homogeneously or non-homogeneously within the nutritional supplement.

A nutritional supplement for jointly elevating growth hormone release and testosterone release may be ingested on a regular basis, such as a daily or weekly intake at a dosage tailored to an individual's needs; i.e., the nutritional supplement is to be taken regularly as multiples (1×, 2×, etc.) of the dosage form (e.g., pills, tablets, capsules, etc.) in accordance with the needs of the individual. For example, a senior citizen leading a sedentary life is likely to need higher daily doses than does a young person engaged in regular strenuous exercise (e.g., a weight lifter).

Alternatively, the nutritional supplement for jointly elevating growth hormone release and testosterone release may be ingested on an as-needed basis at a dosage tailored to the individual's needs. Medical or nutritional counseling may be beneficial for arriving at a desirable or optimal dosage tailored to the individual's needs. The nutritional supplement may be administered, for example, from one to three times daily, or, by way of further example, the supplement may be administered every other day, or once a week. In particular embodiments, the nutritional supplement may be administered on an empty stomach.

In certain embodiments, a nutritional supplement for jointly elevating growth hormone release and testosterone release comprises a particular combination of types of amino acids, mass ranges, and specific formulations that have been selected to be synergistically-balanced and of adequate quantity to achieve a desired physiological effect; e.g., growth hormone release and testosterone release. Improper combinations of the same amino acids may be ineffective. The component amino acids may be synergistic in the sense that several of them, when combined together, synergistically stimulate the release of both human growth hormone and testosterone. The combination of amino acids in particular embodiments was also chosen to reduce or inhibit chemical combination or reaction between the component amino acids.

EXAMPLES

Example 1

Effect of an Oral Nutritional Supplement Single Dose on hGH Levels

The short-term effects of a single oral nutritional supplement on hGH levels 2 hours post ingestion was studied 16 healthy subjects [12 males, 4 females; 9 Caucasian, 6 African American, 1 other; mean age=32±14 years; body mass index=26.4±5.0 ranging from 19.1 to 36.8 kg/m$^2$]. Each subject reported to the Inpatient Unit on two occasions one week apart. After an overnight fast, subjects had an IV line placed and baseline bloods samples were drawn at −30, −15, and 0 minutes.

Subjects were then asked to swallow the capsules of supplement (SeroVital™) or an identical looking placebo. SeroVital™ is a 2.9 g/dose blend of L-lysine HCl, L-arginine HCL, oxo-proline, N-acetyl-L-cysteine, L-glutamine, and schizonepeta (aerial parts) powder. Blood was drawn at 15, 30, 60 and 90 and 120 minutes for assay. Human GH was measured at each time point using the Siemens Immulite™ 2000 (intra-assay CV was 3.72%, inter-assay CV was 5.70%, and the detection limit for GH was 0.05 ng/mL. The −15 and 120 minute time points were additionally assayed for triiodothyronine (T3) as informative for mechanistic investigations.

The mean growth hormone increased 682% after the supplement from 0.17 at baseline to 1.33 ng/mL at 120 minutes, compared to a mean decrease of 52% after the placebo from 0.93 to 0.45 ng/mL. FIG. 1.

The mean change in GH levels from baseline to 120 minutes (GH at 120 minutes minus GH at 0 minutes), was 1.15

(95% CI: 0.17, 2.14) ng/mL after the supplement, versus −0.48 (−1.47, 0.50) ng/mL after the placebo, demonstrating a statistically-significant differential effect (P=0.01). After the supplement, the mean AUC for GH across 120 minutes was 20.43 (95% CI: 19.90, 20.95) ng/mL/min which was significantly higher (P=0.04) than placebo at 19.67 (18.74, 20.59) ng/mL/min. Overall, 120 minutes after taking the supplement, GH levels were significantly higher in absolute levels or by AUC.

As daily circadian levels of T3 naturally decrease during the morning hours, at which the current trial was scheduled, it was not surprising that placebo levels between the −15 and 120 minute time points decreased by −6.10 ng/dL (106 to 100 ng/dL, P=0.01). In contrast, the SeroVital™ group exhibited a deceased reduction in T3 by nearly one-half over the same time course, −3.3 ng/dL (101-97.3 ng/dL, NS), which was not a significant reduction compared to baseline, as was the reduction in the placebo group. These results affirm that somatostatin inhibition plays a mechanistic role in the ability of SeroVital™ to induce significant increases in serum GH levels in human subjects.

At 120 minutes, GH concentrations were 2-fold higher in women (2.3±1.1 ng/mL, n=4) than in men (1.0±0.4 ng/mL, n=12, although the study was not adequately powered for these comparisons. Nevertheless, these findings support an enhanced effect of the SeroVital™ supplement in women.

An eight-fold increase was observed, equivalent to 682%, in GH levels 120 minutes after a single oral supplement of SeroVital™. The study had a broad range of ages and BMI's and included both genders. An additional advantage of the present study over previous GH evaluations is that it contained a placebo control group and was randomized and double-blinded.

These findings demonstrate that a specialized low-dose amino acid supplement can significantly increase short-term GH levels. Future studies will examine whether such increases in GH with oral amino acid supplementation increase fat-free mass and strength. This indeed may be the case, since elderly subjects administered oral GH secretagogues for 6 and 12 months have sustained increases in lean body mass and improved physical function.

The absolute magnitudes of these results are somewhat difficult to directly correlate among past studies, as commercial GH assays use different antibodies to target specific GH epitopes. Therefore, different antibodies and assays are less likely to recognize some specific isoforms and fragments of the GH molecule. This results in variability of the normal range of the GH measurements in different assays. Indeed, the same GH sample measured using different assays can vary 2-3 fold, limiting the ability to compare actual GH levels across studies. Nevertheless, the mean levels of GH reached after the subcutaneous injection of 0.06 IU of HGH in the treatment of GH deficient subjects was 0.4 ng/mL, a value that was clearly in the range of values seen in our study with oral amino acids.

Findings obtained from a randomized, blinded, placebo-controlled study strengthen the evidence that oral administration of amino acids, when compounded properly, can increase GH serum levels, wherein SeroVital™ administration showed an 8-fold increase, equivalent to a 682% increase in GH levels, 120 minutes after a single oral dose. In addition, we elucidate some mechanistic details for these significant GH increases as through somatostatin inhibition, supported by our results on the 120 minute results on T3 levels in the same subjects.

Example 2

Effect of an Oral Nutritional Supplement on Endurance and Fat Metabolism

To test the effect of the nutritional supplement on endurance and fat metabolism, a double-blind clinical study was conducted involving 12 healthy subjects [7 males, 5 females; mean age=31±6 years; body mass index=25.7±3.8 ranging from 20.3 to 32.2 kg/m$^2$]. Each subject reported to the Fitness Testing Facility (PEAK, University of Utah College of Health) after an overnight fast. Upon arrival, each subjects underwent standard measurements of weight, height, body fat percent (Bod Pod), and resting metabolic rate (RMR, indirect calorimerty). Daily calorie expenditure was estimated based on the additive evaluations of measured RMR, estimated Lifestyle and Activity (defined as the number of calories burned performing daily activities including working, playing eating, etc), and estimated Exercise (defined as an estimate of the number of calories burned during exercise based on daily activity level). Following the baseline measurements, subjects then consumed a standard breakfast (Egg McMuffin, 300 Calories; 12 g fat; 29 g carbohydrates; 18 g protein). Subjects rested for a further 45 minutes to reach a post-absorptive state, then underwent a Maximal Aerobic Fitness Test of graded exercise, completed on a treadmill. Subjects' oxygen uptake was measured using a metabolic cart, and $VO_{2max}$ was quantified.

Subjects were then provided a two week supply of a novel supplement SeroVital™ (2.9 g/dose blend of L-lysine HCl, L-arginine HCl, oxo-proline, N-acetyl-L-cysteine, L-glutamine, and schizonepeta (aerial parts) powder). The novel SeroVital™ increases serum human growth hormone hGH levels by 8 times (equivalent to 682%) 120 minutes after a single dose in healthy male and female volunteers. In this study, subjects were instructed to consume one dose of the supplement on an empty stomach, two hours after dinner prior to bedtime, every night for the two-week study duration.

Following the final dose, each subject returned to the PEAK Fitness Testing Facility, University of Utah College of Health after an overnight fast (without having consumed their last dose of the supplement since the previous night). Upon arrival, each subjects underwent the identical test protocols as the baseline test day. The data from the two measurement days were then analyzed. Consistent with the hypothesis that the supplement would increase improve endurance parameters with its ability to increase in hGH levels, the decision was made to reject the null only if the data supported the one directional alternative consistent with a favorable response to the supplement. Statistical significance was assumed for P≤0.05.

Mean $VO_{2max}$ increased by 6% from 44.9±8.1 at baseline to 47.7±9.2 mL/kg/min (3.69±0.96 to 3.91±1.02 L/min), demonstrating a statistically significant differential effect compared to baseline (P=0.02). After the period of supplementation with SeroVital™, the mean RMR increased by 2.7% from 1687±330 to 1733±288 kcal/day with a statistical trend towards significance compared to baseline (P=0.165). Estimated daily calorie expenditure also increased by 2.7% from 1687±330 to 1733±288 kcal/day with the trend towards significance (P=0.166).

After two weeks of supplementation with the supplement SeroVital™, (taken on an empty stomach, two hours after dinner prior to bedtime, every night), both RMR and estimated daily calorie expenditure tended to increase, evidencing the potential of the supplement to impart long-term fat burning effects. Additionally, endurance as measured by $VO_{2max}$ in the post-absorptive state significantly improved with a measured 6% increase. Overall, the SeroVital™ supplement was shown to increase parameters of endurance, energy, and vitality.

Example 3

Effect of an Oral Nutritional Supplement on Sleep Improvement

To test the ability of the nutritional supplement to improve sleep, a double-blind clinical study was conducted involving 15 healthy subjects [10 males, 5 females; mean age=33±7 years]. Each subject completed a baseline Epworth Sleepiness Scale self-report questionnaire and a standardized assay of usual sleep habits. All subjects were deemed to have average sleep parameters within a normal range.

The subjects were then provided a three week supply of a novel supplement SeroVital™ (2.9 g/dose blend of L-lysine HCl, L-arginine HCl, oxo-proline, N-acetyl-L-cysteine, L-glutamine, and schizonepeta (aerial parts) powder). The novel SeroVital™ blend increases serum human growth hormone hGH levels by 8 times (equivalent to 682%) 120 minutes after a single dose in healthy male and female volunteers.

We investigated sleep patterns with continued use of the supplement when taken on an empty stomach, two hours after dinner prior to bedtime, every night for three weeks. On each trial day, subjects reported 1) time went to bed; 2) time of final wakening; 3) estimated time to fall asleep; 4) time of awakening during sleep/length of time awake. Data was compiled by day for estimated time to fall asleep and length of time awake during sleep in order to assess sleep efficiency. Daily values for each measure were plotted as an average (±S.D.) among the subjects over the time course of the study, and a linear regression was tabulated to assess overall trends over time. All available data was included in the analysis.

Figure 2:
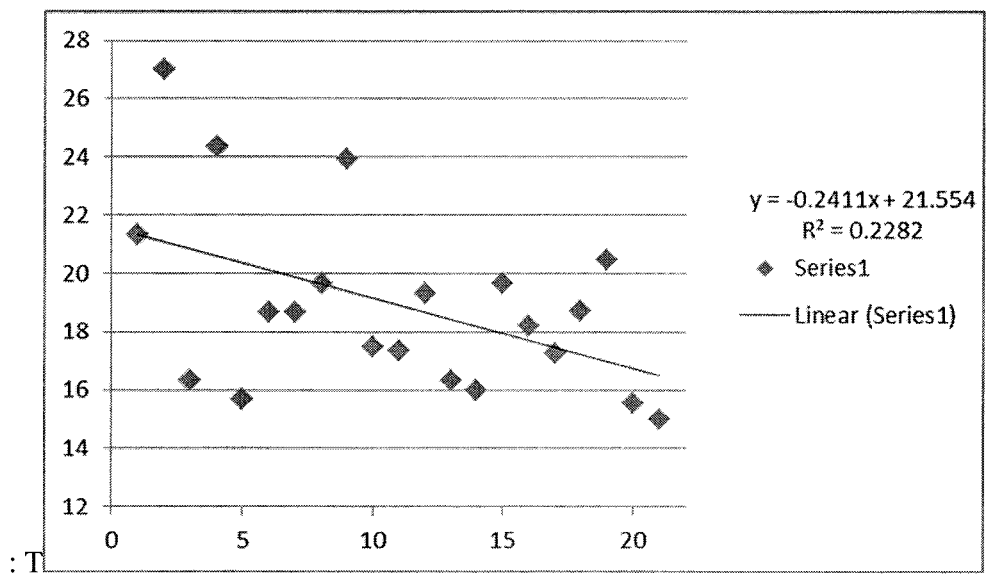
FIG. 2 includes a scatter plot and linear regression analysis of the time to fall asleep in subjects with continued use of an exemplary supplement over time.
Figure 3:
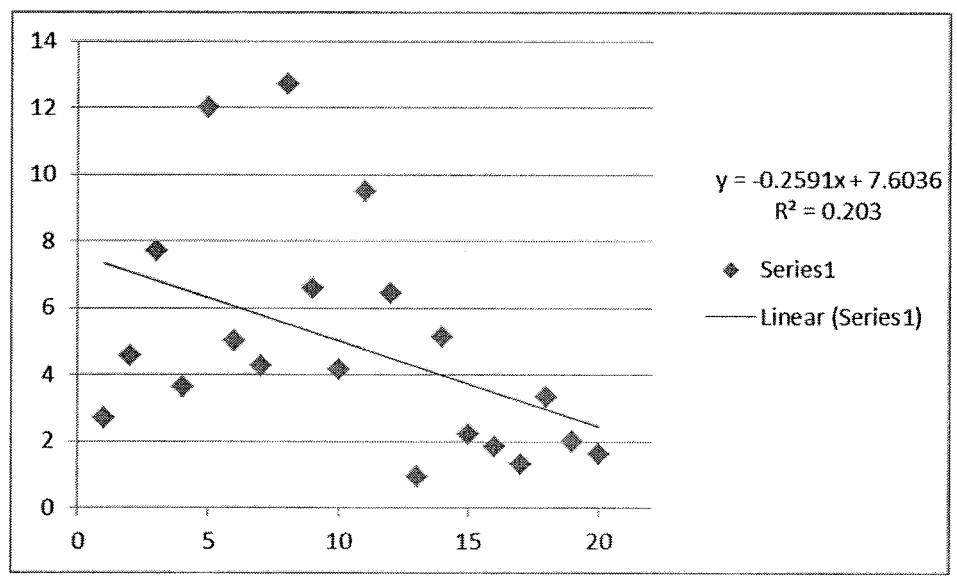
FIG. 3 includes a scatter plot and linear regression analysis of the time awake during sleep over time in subjects with continued use of an exemplary supplement.

Linear regression analysis showed that both estimated time to fall asleep (FIG. 2) and time awake during sleep (FIG. 3) tended to decrease over time with continued use of the supplement over the time course of the study. The time to fall asleep decreased with an average slope of −0.24 min/day, and the time awake during sleep decreased by an average slope of −0.26 min/day. Overall, these results so a trend towards greater sleep efficiency by measurements of both time to fall asleep and time awake during sleep, both with a quantified average decrease of about 0.25 min/day over three weeks with regular nighttime use of the novel SeroVital™ supplement (when taken as directed, on an empty stomach, two hours after dinner prior to bedtime).

Example 4

Effect of an Oral Nutritional Supplement on Lean Body Mass and Weight Change

To test the effect of the nutritional supplement on lean body mass and weight change of humans, healthy men and women between the ages of 30 to 80 years are recruited through advertisements. Standardized assessment criteria are used to select subjects at risk for functional decline (e.g., hand grip strength, habitual gait speed, etc.). Additionally, subjects are excluded for diabetes mellitus, use of anticoagulants, seizure disorder, cancer treatment within five years, poorly controlled hypertension, unstable or recent onset angina, myocardial infarction within 6 months, cognitive impairment, depression, significant limitations of lower extremity function, bradycardia, systolic blood pressure <100 or >170 mm Hg, or orthostatic hypotension. Subjects participating in strength training programs were also excluded.

Subjects are given daily doses of the nutritional supplement for 6 months at different dosing concentrations of active ingredients, and one group is treated as a placebo group. The study includes a pre-screening assessment, screening and baseline visits, and weekly visits over the planned 6 months, where weight, body composition, and physical performance (including endurance) are determined, along with hormonal data analysis. Weight, percent lean body mass, and percent fat body mass are chosen as primary measures of body composition at the 6 month analysis period.

Example 5

Effect of an Oral Nutritional Supplement on Energy, Bone Density, Skin Thickness, and Mass of Adipose Tissue To test the effect of the nutritional supplement on energy, bone density, skin thickness, and mass of adipose tissue of healthy men over 60 years old are recruited through advertisements. Standardized assessment criteria are used to select subjects at risk for functional decline (e.g., hand grip strength, habitual gait speed, etc.). Entry criteria includes body weight of 90 to 120 percent of the standard for age. Additionally, subjects are excluded for diabetes mellitus, use of anticoagulants, seizure disorder, cancer treatment within five years, poorly controlled hypertension, unstable or recent onset angina, myocardial infarction within 6 months, cognitive impairment, depression, significant limitations of lower extremity function, bradycardia, systolic blood pressure <100 or >170 mm Hg, or orthostatic hypotension. Subjects participating in strength training programs were also excluded.

Subjects are given daily doses of the nutritional supplement for 6 months at different dosing concentrations of active ingredients, and one group is treated as a placebo group. The study includes a pre-screening assessment, screening and baseline visits, and weekly visits over the planned 6 months, where lean body mass, mass of adipose tissue, skin thickness, and bone density at various skeletal sites are measured. Subjects are also monitored for changes in energy levels throughout the experiment.

Example 6

Effect of an Oral Nutritional Supplement on Anxiety and Sleep

To test the effect of the nutritional supplement on anxiety and sleep, healthy men and women between the ages of 30 to 80 years are recruited through advertisements. Subjects are interviewed by a psychiatrist using the Structured Clinical Interview for DSM-III-R or analogous method. Patients are all drug free. The study focuses on the evaluation of anxiety, sleep patterns, and measurement of basal morning stress hormone levels at various points during the 6 month testing period.

Subjects are given daily doses of the nutritional supplement for 6 months at different dosing concentrations of active ingredients, and one group are treated as a placebo group. The study includes a pre-screening assessment, screening and baseline visits, and weekly visits over the planned 6 months, where anxiety assessment (e.g., Hamilton Anxiety Rating Scale), and anxiety and stress hormone levels (e.g., cortisol and GH) are determined, and sleep study analysis are conducted.

Example 7

Effect of an Oral Nutritional Supplement on Testosterone Levels

The effects of an oral nutritional supplement on testosterone levels are studied in a group of healthy human subjects. Subjects are asked to swallow the capsules of SeroVital™, or an identical looking placebo.

Blood samples (8-10 mL) are taken from each participant before use, after 6 days of use, after 12 days of use, and 3 days after suspending use. Each blood draw is taken in the morning between 9:30 and 10:30 am, at a time when serum oscillations of testosterone is at its minimum daily value. The determination of testosterone in human blood is carried out using commercially available immunochemoluminescence assays. (Topo et al., 2009)

Results on testosterone release show that after using the SeroVital™ supplement, serum testosterone levels are increased in a significant number of the subjects taking the supplement. On average, the increase in serum testosterone is statistically significant compared to those of the placebo group over the time course of the study.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

We claim:

1. A method for increasing sex steroids and human growth hormone in a human being in need thereof, the method comprising:
providing an oral nutritional supplement unit dosage form, wherein the oral nutritional supplement unit dosage form comprises about 1 mmol L-arginine, about 1 mmol Oxo-proline, about 2 mmol L-lysine, about 1.5 µmol N-acetyl L-cysteine, about 2 µmol L-glutamine, and about 125 µg Schizonepta (aerial parts) powder; and
orally administering an effective amount of the nutritional supplement to the human being.

2. The method according to claim 1, wherein the oral nutritional supplement unit dosage form comprises:
about 0.9 mmol L-arginine,
about 1.3 mmol Oxo-proline,
about 2.0 mmol L-lysine,
about 1.5 µmol N-acetyl L-cysteine,
about 1.7 µmol L-glutamine, and
about 1.25 µg Schizonepta (aerial parts) powder.

3. The method according to claim 2, wherein the oral nutritional supplement unit dosage form comprises about 181 mg L-arginine HCl; about 170 mg L-pyroglutamic acid; about 374 mg L-lysine HCl; about 0.25 mg N-acetyl L-cysteine USP; about 0.25 mg L-glutamine, and about 0.125 mg Schizonepta (aerial parts) powder.

4. The method according to claim 1, wherein the oral nutritional supplement unit dosage form is administered to the human being, so as to increase lean body mass or libido; reduce obesity, adipose tissue mass, or anxiety; support weight loss; decrease appetite and atrophic processes in skeletal muscle, liver, kidney, spleen, skin, or bone; improve energy, endurance, sleep, metabolism, heart rate, blood pressure, cardiovascular health, sympathetic nervous activity, thyroid response, fat metabolism, glucose utilization, mental/cognitive function, reaction time, bone density, hair health and appearance, nail health and appearance, skin health and appearance, or libido; and/or affect one or more condition(s) and/or disease(s) that depend upon androgen activity in the human being.

5. The method according to claim 1, wherein the oral nutritional supplement unit dosage form is orally administered in a total amount of about 2.9 grams.

6. The method according to claim 1, wherein the oral nutritional supplement is administered from one to three times daily.

7. The method according to claim 1, wherein the oral nutritional supplement is administered once a week.

8. The method according to claim 1, wherein the human being is at least 30 years old.

9. The method according to claim 1, wherein the human being exhibits one or more symptoms of post-traumatic stress disorder selected from the group consisting of re-experiencing the original trauma(s) through flashbacks or nightmares, avoidance of stimuli associated with the trauma, increased arousal, difficulty falling or staying asleep, anger, and hypervigilance.

* * * * *